US007947693B2

(12) United States Patent
Nordvall et al.

(10) Patent No.: US 7,947,693 B2
(45) Date of Patent: May 24, 2011

(54) 5,7-DISUBSTITUTED THIAZOLO[4,5-D]PYRIMIDINES AS CHEMOKINE INHIBITORS

(75) Inventors: Gunnar Nordvall, Sodertalje (SE); Colin Ray, Sodertalje (SE); Tobias Rein, Sodertalje (SE); Daniel Sohn, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 531 days.

(21) Appl. No.: 11/910,780

(22) PCT Filed: Apr. 3, 2006

(86) PCT No.: PCT/SE2006/000399
§ 371 (c)(1),
(2), (4) Date: Oct. 5, 2007

(87) PCT Pub. No.: WO2006/107258
PCT Pub. Date: Oct. 12, 2006

(65) Prior Publication Data
US 2008/0214578 A1    Sep. 4, 2008

(30) Foreign Application Priority Data
Apr. 6, 2005  (SE) ..................... 0500767

(51) Int. Cl.
*C07D 487/04* (2006.01)
*A61K 31/519* (2006.01)
*A61P 11/06* (2006.01)
*A61P 9/10* (2006.01)
*A61P 37/06* (2006.01)

(52) U.S. Cl. .................... 514/260.1; 544/255
(58) Field of Classification Search .............. 544/255; 514/260.1
See application file for complete search history.

(56) References Cited

U.S. PATENT DOCUMENTS

| | | | |
|---|---|---|---|
| 2,772,164 A | 11/1956 | Allen et al. | |
| 4,639,433 A | 1/1987 | Hunt et al. | |
| 4,643,987 A | 2/1987 | Nagarajan et al. | |
| 4,698,327 A | 10/1987 | Nagarajan et al. | |
| 5,202,328 A | 4/1993 | de Laszlo et al. | |
| 5,591,714 A | 1/1997 | Nagarajan et al. | |
| 5,840,684 A | 11/1998 | Cooper et al. | |
| 6,107,294 A | 8/2000 | Beck | |
| 6,790,850 B1 * | 9/2004 | Willis et al. | 514/260.1 |
| 6,806,273 B1 | 10/2004 | Austin et al. | |
| 7,067,657 B2 | 6/2006 | Hanson et al. | |
| 2003/0107189 A1 | 6/2003 | Bonnert et al. | |
| 2006/0211982 A1 * | 9/2006 | Prestrelski et al. | 604/60 |
| 2007/0142386 A1 | 6/2007 | Nordvall et al. | |

FOREIGN PATENT DOCUMENTS

| | | |
|---|---|---|
| EP | 0435503 A1 | 5/1999 |
| WO | 9956760 A1 | 11/1999 |
| WO | 0009511 A1 | 2/2000 |
| WO | 0158906 A1 | 8/2001 |
| WO | 0158907 | 8/2001 |
| WO | 0162758 A1 | 8/2001 |
| WO | 02076990 A1 | 10/2002 |
| WO | 02083693 A1 | 10/2002 |
| WO | 2005033115 A1 | 4/2005 |

OTHER PUBLICATIONS

Baxter et al. (Bioorg. Med. Chem. Lett., 2006, 16(4), pp. 960-963).*
Baker, et al, "Synthesis of Derivatives of Thiazolo . . . ," J. Chem. Soc., pp. 2478-2484 (1970).
Balabanian, et al., "CX3C Chemokine Fractalkine in Pulmonary Arterial Hypertension," Am. J. Respir .Cnt. Care Med.165, 1419-1425 (2002).
Chapman, et al., "Fractalkine Cleavage from Neuronal Membranes Represents an Acute Event in the Inflammatory Response to Excitotoxic Brain Damage," J. Neuroscience 20, 1-5 (2000).
Cooper, et al, J Antibiotics, 49:6, 575-581 (1996) "Reductive Alkylation of Glycopeptide Antibiotics: Synthesis and Antibacterial Activity".
Maggiolo, et al, "Studies on Condensed Pyrimidine Systems . . . ," J. Amer. Chem.. Soc., vol. 73, pp. 4226-4228 (1951).
Moatti, et al, "Polymorphism in the Fractalkine Receptor CX3CRI as a Genetic Risk Factor for Coronary Artery Disease," Blood 97, 1925-1928 (2001).
Nagarajan, et al, J. Antibiotics, 41:10, 1430-1438 (1988) "Synthesis and Antibacterial Activity of N-acyl Vancomycins".
Ruth, et al., "Fractalkine, a Novel Chemokine in Rheumatoid Arthritis and in Rat Adjuvant-Induced Arthritis," Arthritis Rheum. 44,1568-1581 (2001).
Soriano, et al., "Mice Deficient in Fractalkine are less Susceptible to Cerebral Ischemia-ReperfusionInjury," J. Neuroinununol, 125, 59-65 (2002).
Takahashi, et al, "Studies on Pyrimidine Derivatives . . . ," Chem. Pharm. Bull, vol. 6, pp. 334-338 (1958).
Tarozzo, et al., "Expression of Fractalkine and its Receptor, CX3CR1, in Response to Ischaemia-Reperfusion Brain Injury in the Rat," Eur. J. Neuroscience 15,1663-1668 (2002).
Twining, et al., "Spinal Fractalkine Induces Allodynia & Hyperalgesia," Society for Neuroscience 27, 732,Abstract No. 279.12 (2001).
Umehara, et al., Arterioscler Thromb Vasc Biol. Jan. 2004;24(1)34-40, Epub Sep. 11, 2003.
Umehara, et al., "Fractalkine and Vascular Injury," Trends Immunol . 22,602-607 (2001).

(Continued)

*Primary Examiner* — Susanna Moore
(74) *Attorney, Agent, or Firm* — Connolly Bove Lodge & Hutz LLP

(57) ABSTRACT

There are disclosed novel 5-substituted 7-amino-[1,3]thiazolo[4,5-d]pyrimidine derivatives of formula (I) wherein $R^1$, $R^2$, $R^3$, $R^4$ and $R^5$ are as defined in the specification, and pharmaceutically acceptable salts thereof, together with processes for their preparation, pharmaceutical compositions comprising them and their use in therapy. The compounds of formula (I) are $CX_3CR1$ receptor antagonists and are thereby particularly useful in the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

8 Claims, No Drawings

OTHER PUBLICATIONS

Verge, et al., "Mapping Fractalkine and its Receptor (CX3CRI) in a Rat Model of InflammatoryNeuropathy," IASP Abstract No. 393-P27 (2002).

Volin, et al., "Fractalkine : A Novel Angiogenic Chemokine in Rheumatoid Arthritis," Am J. Pathology159,1521-1530 (2001).

Watkins, et al., "Spinal Fractalkine : KeyPlayer in Exaggerated Pain States," IASP Abstract No. 390-P24(2002).

Zujovic, et al., "Fractalkine Modulates TNF-alpha Secretion and Neurotoxicity Induced byMicroglial Activation," GLIA 29, 305-315 (2000).

Pfleiderer, et al., "Pteridine, XXVII 1) Synthese and Struktur von 7-Hydroxy-isopterinen", Chemische Berichte, 1963, vol. 96, No. 11, p. 2964-2976, Table 2, Compound 5.

STN International, file CA, Chem Abstracts, vol. 60, Pfleiderer, et al: "Original Ref. No. 60:5486h. Synthesis and Structure of 7-Hydroxyisopterines", Abstract No. 30913, 1963.

STN Int'l, file CAPLUS accession No. 1996-243961, Gewald, et al, "New Synthesis of substituted . . . .,"(1996).

STN Int'l, file CAPLUS accession No. 1990-235252, Ahluwalia, et al, "One step synthesis of thiazolo . . . ," (1989).

STN Int'l, file CAPLUS accession No. 1990-158124, Pawar, et al, "Studies on the Vilsmeier-Haak reaction . . . ," (1989).

\* cited by examiner

5,7-DISUBSTITUTED THIAZOLO[4,5-D]PYRIMIDINES AS CHEMOKINE INHIBITORS

CROSS-REFERENCE TO RELATED APPLICATIONS

This application is a US National Stage under 35 U.S.0 § 371 of International Application No. PCT/SE2006/000399 (filed Apr. 3, 2006) that claims priority under 35 U.S.C. Section 119(a)-(d) to Swedish Application No. 0500767-9 filed on Apr. 6, 2005 in Sweden.

FIELD OF THE INVENTION

The present invention discloses novel 5-substituted 7-amino-[1,3]thiazolo[4,5-d]pyrimidine derivatives together with processes for their preparation, pharmaceutical formulations comprising them and their use in therapy.

BACKGROUND OF THE INVENTION

Chemokines play an important role in immune and inflammatory responses in various diseases and disorders, including asthma, atherosclerosis and allergic diseases, as well as autoimmune pathologies such as rheumatoid arthritis and multiple sclerosis. These small, secreted molecules are a growing superfamily of 8-14 kDa proteins characterised by a conserved cysteine motif. At the present time, the chemokine superfamily comprises four groups exhibiting characteristic structural motifs, the C—X—C, C—C and C—$X_3$—C and XC families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues. In contrast, members of the XC family lack one of the first two cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes, lymphocytes and neutrophils. Examples include human monocyte chemotactic proteins 1-3 (MCP-1, MCP-2 and MCP-3), RANTES (Regulated on Activation, Normal T-cell-Expressed and Secreted), eotaxin and the macrophage inflammatory proteins 1α and 1β (MIP-1α and MIP-1β).

The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family. These receptors represent good targets for drug development since agents that modulate these receptors would be useful in the treatment of disorders and diseases such as those mentioned above.

WO 00/09511 discloses certain 2-substituted 4-aminothiazolopyrimidine derivatives that are useful as antagonists of receptors linked to the C—X—C and C—C chemokine families, particularly as antagonists of the CXCR2 receptor.

The present invention relates to a group of compounds that are partly within the generic scope of WO 00/09511 but are of a structural type not specifically exemplified therein. When compared to the Examples disclosed in WO 00/09511, the compounds of the present invention display surprisingly useful properties as antagonists of the $CX_3CR1$ receptor.

DISCLOSURE OF THE INVENTION

The present invention provides compounds of formula (I)

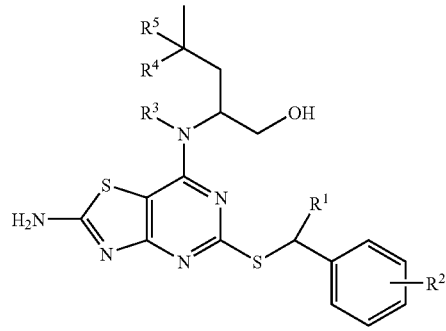

(I)

wherein:
$R^1$ represents $CH_3$ or $CH_3CH_2$;
$R^2$ represents H, 2-F, 2-Cl, 3-F, 3-$OCH_3$, 3-CN, 3-$CF_3$, 3-$CONH_2$ or 3-$SO_2CH_3$;
$R^3$ represents H or $CH_3$;
$R^4$ represents H or $CH_3$; and
$R^5$ represents H; or, when $R^4$ is $CH_3$, $R^5$ represents H or F; and pharmaceutically acceptable salts thereof.

The compounds of formula (I) may exist in stereoisomeric and/or tautomeric forms. It is to be understood that all enantiomers, diastereomers, racemates, tautomers and mixtures thereof are included within the scope of the invention.

In one embodiment, $R^1$ represents $CH_3$. In another embodiment, $R^1$ represents $CH_3CH_2$.

In one embodiment, $R^2$ represents H, 2-F, 3-F, 2-Cl, 3-$OCH_3$, 3-CN or 3-$CF_3$. In another embodiment, $R^2$ represents H, 2-F or 3-CN. In another embodiment, $R^2$ represents H. In another embodiment, $R^2$ represents 2-F. In another embodiment, $R^2$ represents 3-CN.

In one embodiment, $R^3$ represents H.

In one embodiment, $R^4$ represents $CH_3$. In another embodiment, $R^4$ represents H.

In one embodiment, $R^5$ represents H.

In one embodiment, $R^4$ represents $CH_3$ and $R^5$ represents F.
In one embodiment, $R^4$ represents $CH_3$ and $R^5$ represents H.

In one embodiment, $R^1$ represents $CH_3$; $R^2$ represents H, 2-F, 3-F, 2-Cl, 3-$OCH_3$, 3-CN or 3-$CF_3$; $R^3$ represents H; $R^4$ represents H or $CH_3$; and $R^5$ represents H.

In another embodiment, $R^1$ represents $CH_3$; $R^1$ represents H, 2-F or 3-CN; $R^3$ represents H; $R^4$ represents H or $CH_3$; and $R^5$ represents H.

In another embodiment, $R^1$ represents $CH_3$; $R^2$ represents H, 2-F or 3-CN; $R^3$ represents H; $R^4$ represents H; and $R^5$ represents H.

In another embodiment, $R^1$ represents $CH_3$; $R^2$ represents H, 2-F or 3-CN; $R^3$ represents H; $R^4$ represents $CH_3$; and $R^5$ represents H or F.

In another embodiment, $R^1$ represents $CH_3$; $R^2$ represents H; $R^3$ represents H; $R^4$ represents $CH_3$; and $R^5$ represents H.

Particular compounds of formula (I) include:

(2R)-2-[(2-amino-5-{[(1S)-1-(2-fluorophenyl)ethyl]thio}[1,3]thiazolo[4,5-d]pyrimidin-7-yl)amino]pentan-1-ol;

(2R)-2-[(2-amino-5-{[(1S)-1-(2-fluorophenyl)ethyl]thio}[1,3]thiazolo[4,5-d]pyrimidin-7-yl)amino]-4-methylpentan-1-ol;

(2R)-2-({2-amino-5-[(1-phenylethyl)thio][1,3]thiazolo[4,5-d]pyrimidin-7-yl}amino)-4-methylpentan-1-ol;

(2R)-2-[(2-amino-5-{[(1R)-1-phenylethyl]thio}[1,3]thiazolo[4,5-d]pyrimidin-7-yl)amino]-4-methylpentan-1-ol;

3-{(1S)-1-[(2-amino-7-{[(1R)-1-(hydroxymethyl)butyl]amino}[1,3]thiazolo[4,5-d]pyrimidin-5-yl)thio]ethyl}benzonitrile;

(2R)-2-{[2-amino-5-({(1S)-1-[3-(methylsulfonyl)phenyl]ethyl}thio)[1,3]thiazolo[4,5-d]pyrimidin-7-yl]amino}-4-methylpentan-1-ol;

(2R)-2-[(2-amino-5-{[(1s)-1-phenylethyl]thio}[1,3]thiazolo[4,5-d]pyrimidin-7-yl)amino]pentan-1-ol;

3-{(1S)-1-[(2-amino-7-{[(1R)-1-(hydroxymethyl)-3-methylbutyl]amino}[1,3]thiazolo[4,5-d]pyrimidin-5-yl)thio]ethyl}benzonitrile;

(2R)-2-({2-amino-5-[(1-phenylpropyl)thio][1,3]thiazolo[4,5-d]pyrimidin-7-yl}amino)-4-methylpentan-1-ol;

3-{1-[(2-amino-7-{[(1R)-1-(hydroxymethyl)-3-methylbutyl]amino}[1,3]thiazolo[4,5-d]pyrimidin-5-yl)thio]ethyl}benzamide;

(2R)-2-{[2-amino-5-({1-[3-(trifluoromethyl)phenyl]ethyl}thio)[1,3]thiazolo[4,5-d]pyrimidin-7-yl]amino}-4-methylpentan-1-ol;

(2R)-2-[{2-amino-5-[(1-phenylethyl)thio][1,3]thiazolo[4,5-d]pyrimidin-7-yl}(methyl)amino]-4-methylpentan-1-ol;

(2R)-2-[(2-amino-5-{[1-(2-chlorophenyl)ethyl]thio}[1,3]thiazolo[4,5-d]pyrimidin-7-yl)amino]-4-methylpentan-1-ol;

(2R)-2-[(2-amino-5-{[1-(3-methoxyphenyl)ethyl]thio}[1,3]thiazolo[4,5-d]pyrimidin-7-yl)amino]-4-methylpentan-1-ol;

(2R)-2-[(2-amino-5-{[(1S)-1-phenylethyl]thio}[1,3]thiazolo[4,5-d]pyrimidin-7-yl)amino]-4-methylpentan-1-ol;

(2R)-2-[(2-amino-5-{[(1s)-1-phenylethyl]thio}[1,3]thiazolo[4,5-d]pyrimidin-7-yl)amino]-4-fluoro-4-methylpentan-1-ol;

(2R)-2-[(2-amino-5-{[(1S)-1-(2-fluorophenyl)ethyl]thio}[1,3]thiazolo[4,5-d]pyrimidin-7-yl)amino]-4-fluoro-4-methylpentan-1-ol;

(2R)-2-[(2-amino-5-{[(1s)-1-(3-fluorophenyl)ethyl]thio}[1,3]thiazolo[4,5-d]pyrimidin-7-yl)amino]-4-methylpentan-1-ol;

and pharmaceutically acceptable salts thereof.

When compared to the compounds disclosed in WO 00/09511, the compounds of the present invention are characterised by the presence of the branched thiobenzyl group at the 5-position of the thiazolopyrimidine ring system. That is, the compounds of the present invention incorporate a $R^1$ group that is not hydrogen.

According to the invention, we further provide a process for the preparation of a compound of formula (I), or a pharmaceutically acceptable salt thereof which comprises:

a) reacting a compound of formula (II):

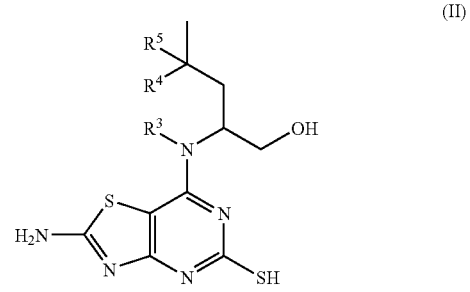

(II)

wherein $R^3$, $R^4$ and $R^5$ are as defined in formula (I);
with a compound of formula (III):

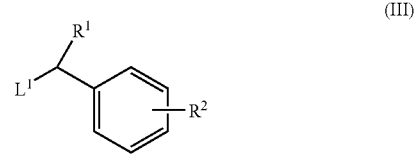

(III)

wherein $R^1$ and $R^2$ are as defined in formula (I) and $L^1$ represents a leaving group; or b) reacting a compound of formula (IV)

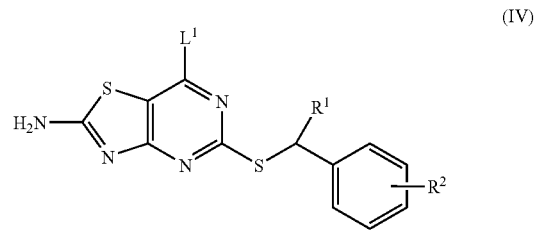

(IV)

wherein $R^1$ and $R^2$ are as defined in formula (I) and $L^2$ represents a leaving group;
with a compound of formula (V)

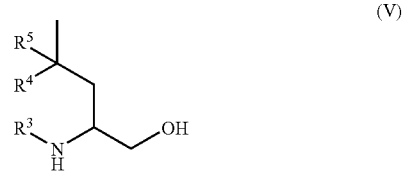

(V)

wherein $R^3$, $R^4$ and $R^5$ are as defined in formula (I);
and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), the reactants (II) and (III) are coupled together in a suitable organic solvent such as dimethylsulfoxide (DMSO), acetonitrile or 1-methyl-2-pyrrolidinone (NMP). The reaction is optionally performed in the presence of an added organic or inorganic base such as triethylamine, N,N-diisopropylethylamine (DIPEA) or sodium hydride. The reaction is optionally performed in the presence of a mild reducing agent such a sodium borohydride. The reaction is conducted at a suitable temperature, normally between room temperature and the boiling point of the solvent. The reaction is generally continued for a period of about one hour to one week, or until analysis indicates that formation of the required product is complete.

In process (b), the reactants (IV) and (V) are coupled together in a suitable organic solvent such as tetrahydrofuran, acetonitrile, dimethylsulphoxide or 1-methyl-2-pyrrolidinone. The reaction is optionally performed in the presence of an added base. This base may be an organic base such as triethylamine or N,N-diisopropylethylamine, or an inorganic base such as potassium carbonate. The reaction is conducted at a suitable temperature, normally between room temperature and the boiling point of the solvent, but optionally at higher temperatures if a sealed reaction vessel is used. The reaction is generally continued for a period of about one hour to one week, or until analysis indicates that formation of the required product is complete.

Suitable leaving groups $L^1$ and $L^2$ are halogen, particularly chloro or bromo. In one embodiment, $L^1$ and $L^2$ each represent chloro.

It will be apparent to a person skilled in the art that in the above processes it may be desirable or necessary to protect an amine, hydroxyl or other potentially reactive group. Suitable protecting groups and details of processes for adding and removing such groups are, in general, well known in the art. See, for example, "Protective Groups in Organic Synthesis", 3rd Edition (1999) by Greene and Wuts.

The present invention includes compounds of formula (I) in the form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question.

Salts of compounds of formula (I) may be formed by reacting the free compound, or a salt, enantiomer or racemate thereof, with one or more equivalents of the appropriate acid or base. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) are either known from WO 00/09511 or may be prepared using known methods that will be readily apparent to the man skilled in the art.

Compounds of formula (IV) may be prepared using methods analogous to those disclosed in WO 00/09511, or using other known methods that will be readily apparent to the man skilled in the art.

Compounds of formulae (III) and (V) are either commercially available, or known in the literature, or may be prepared using known methods that will be readily apparent to the man skilled in the art.

Suitable specific methods for the preparation of compounds of formulae (II), (III), (IV) and (V) are detailed in the Examples section of the present application and such methods represent specific embodiments of the processes of the invention.

For example, compounds of formula (II), and thence those of formula (I), may be prepared as shown in Scheme 1:

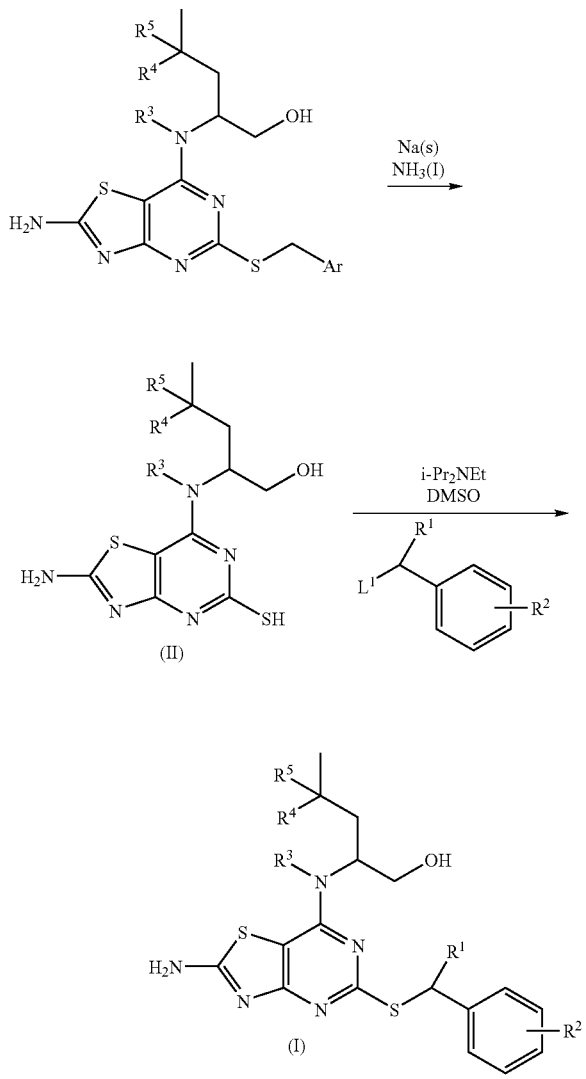

Intermediate compounds may be used as such or in protected form. Suitable protecting groups and details of processes for adding and removing such groups are, in general, well known in the art. See, for example, "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula (I) may exist in stereoisomeric forms. Therefore, all enantiomers, diastereomers, racemates and mixtures thereof are included within the scope of the invention. The various optical isomers may be isolated by separation of a stereoisomeric mixture of the compounds using conventional techniques, for example, fractional crystallisation, or HPLC. Alternatively, the various optical isomers may be prepared directly using optically active starting materials.

The compounds of formula (I) contain two stereogenic centres and may thus exist in four discrete stereoisomeric forms as shown in formulae (Ia) to (Id)

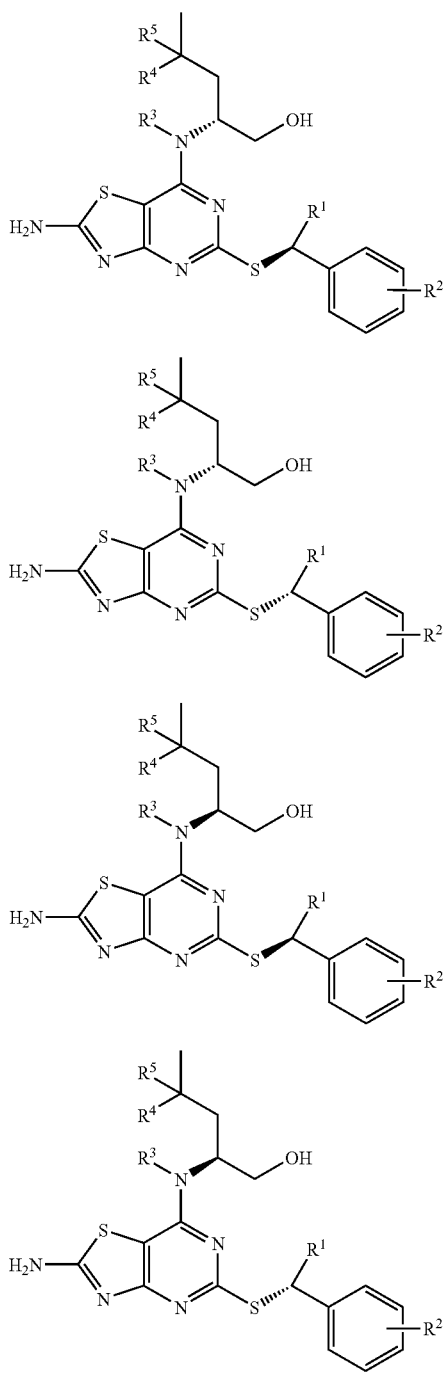

All such four stereoisomers and any mixtures thereof are included within the scope of the invention. In one embodiment, the compounds of formula (I) have the stereochemistry shown in formula (Ia). In another embodiment, the compounds of formula (I) have the stereochemistry shown in formula (Ib).

Intermediate compounds may also exist in stereoisomeric forms and may be used as purified enantiomers, diastereomers, racemates or mixtures.

The compounds of formula (I), and their pharmaceutically acceptable salts are useful because they possess pharmacological activity as antagonists of the $CX_3CR1$ receptor. In particular, when compared to the compounds specifically exemplified in WO 00/09511, the compounds of formula (I) of the present invention possess significantly improved potencies for inhibition of the $CX_3CR1$ receptor and/or decreased potencies for inhibition of the CXCR2 receptor. Preferred compounds of the present invention display both enhanced potency for the inhibition of $CX_3CR1$ and decreased potency for inhibition of CXCR2.

In one aspect the present invention provides a compound of formula (I) or a pharmaceutically acceptable salt thereof, for use as a medicament.

In another aspect the present invention provides the use of a compound of formula (I) or a pharmaceutically acceptable salt thereof, in the manufacture of a medicament, for the treatment or prophylaxis of diseases or conditions in which antagonism of the $CX_3CR1$ receptor is beneficial.

In another aspect the present invention provides the use of a compound of formula (I) or a pharmaceutically acceptable salt thereof, in the manufacture of a medicament, for the treatment or prophylaxis of neurodegenerative disorders, demyelinating disease, cardio- and cerebrovascular atherosclerotic disorders, peripheral artery disease, rheumatoid arthritis, pulmonary diseases such as COPD, asthma or pain.

In another aspect the present invention provides the use of a compound of formula (I) or a pharmaceutically acceptable salt thereof, in the manufacture of a medicament, for the treatment or prophylaxis of multiple sclerosis (MS).

In another aspect the present invention provides the use of a compound of formula (I) or a pharmaceutically acceptable salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

In another aspect the present invention provides the use of a compound of formula (I) or a pharmaceutically acceptable salt thereof, in the manufacture of a medicament, for the treatment or prophylaxis of atherosclerosis by changing the composition of the plaques to reduce the risk of plaque rupture and atherothrombotic events.

According to the invention, there is also provided a method of treating, or reducing the risk of, diseases or conditions in which antagonism of the $CX_3CR1$ receptor is beneficial which comprises administering to a person suffering from or at risk of, said disease or condition, a therapeutically effective amount of a compound of formula (I) or a pharmaceutically acceptable salt thereof.

There is also provided a method of treating, or reducing the risk of, neurodegenerative disorders, demyelinating disease, cardio- and cerebrovascular atherosclerotic disorders, peripheral artery disease, rheumatoid arthritis, pulmonary diseases such as COPD, asthma or pain in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of, multiple sclerosis (MS) in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of a compound of formula (I) or a pharmaceutically acceptable salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of formula (I) or a pharmaceutically acceptable salt thereof.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of diseases or conditions in which antagonism of the $CX_3CR1$ receptor is beneficial.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of neurodegenerative disorders, demyelinating disease, cardio- and cerebrovascular atherosclerotic disorders, peripheral artery disease, rheumatoid arthritis, COPD, asthma or pain.

In another aspect the invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of multiple sclerosis.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of formula (I), or a pharmaceutically acceptable salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

The compounds of formula (I) and their pharmaceutically acceptable salts are indicated for use in the treatment or prophylaxis of diseases or conditions in which modulation of activity at the $CX_3CR1$ receptor is desirable. In particular, the compounds are indicated for use in the treatment of neurodegenerative disorders or demyelinating disease in mammals including man. More particularly, the compounds are indicated for use in the treatment of multiple sclerosis. The compounds are also indicated to be useful in the treatment of pain, rheumatoid arthritis, osteoartritis, cardio- and cerebrovascular atherosclerotic disorders, peripheral artery disease and pulmonary arterial hypertension.

Conditions that may be specifically mentioned are: neurodegenerative diseases and dementia disorders, for example, Alzheimer's disease, amyotrophic lateral sclerosis and other motor neuron diseases, Creutzfeldt-Jacob's disease and other prion diseases, HIV encephalopathy, Huntington's disease, frontotemporal dementia, Lewy body dementia and vascular dementia; polyneuropathies, for example, Guillain-Barré syndrome, chronic inflammatory demyelinating polyradiculoneuropathy, multifocal motor neuropathy and plexopathies; CNS demyelination, for example, acute disseminated/haemorrhagic encephalomyelitis and subacute sclerosing panencephalitis; neuromuscular disorders, for example, myasthenia gravis and Lambert-Eaton syndrome; spinal disorders, for example, tropical spastic paraparesis and stiff-man syndrome; paraneoplastic syndromes, for example, cerebellar degeneration and encephalomyelitis; traumatic brain injury; migraine; cancer; allograft rejection; systemic sclerosis; viral infections; parasite-transmitted diseases, for example, malaria; periodontal disease; myocardial infarction; stroke; coronary heart disease; ischaemic heart disease; restenosis; rheumatoid arthritis; pulmonary diseases such as COPD; asthma or pain.

The compounds of the invention are also indicated for use in the treatment of atherosclerosis by preventing and/or reducing the formation of new atherosclerotic lesions or plaques and/or by preventing or slowing progression of existing lesions and plaques.

The compounds of the invention are also indicated for use in the treatment of atherosclerosis by changing the composition of the plaques so as to reduce the risk of plaque rupture and atherothrombotic events.

The compounds of the invention are also indicated for use in the treatment of inflammatory bowel disease (IBD), for example, Crohn's disease and ulcerative colitis, by inducing remission and/or maintaining remission of IBD.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I) and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition that comprises mixing the ingredients.

The invention further relates to combination therapies wherein a compound of formula (I) or a pharmaceutically acceptable salt thereof, or a pharmaceutical composition or formulation comprising a compound of formula (I), is administered concurrently or sequentially with therapy and/or an agent for the treatment of any one of cardio- and cerebrovascular atherosclerotic disorders and peripheral artery disease.

In particular, a compound of formula (I) or a pharmaceutically acceptable salt thereof may be administered in association with compounds from one or more of the following groups:
1) anti-inflammatory agents, for example,
    a) NSAIDs (e.g. acetylsalicylic acid, ibuprofen, naproxen, flurbiprofen, diclofenac, indometacin);
    b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
    c) leukotriene receptor antagonists; (e.g. CP195543, amelubant, LY293111, accolate, MK571);
2) anti-hypertensive agents, for example,
    a) beta-blockers (e.g. metoprolol, atenolol, sotalol);
    b) angiotensin converting enzyme inhibitors (e.g. captopril, ramipril, quinapril, enalapril);
    c) calcium channel blockers (e.g. verapamil, diltiazem, felodipine, amlodipine);
    d) angiotensin II receptor antagonists (e.g. irbesartan, candesartan, telemisartan, losartan);
3) anti-coagulantia, for example,
    a) thrombin inhibitors (e.g. ximelagatran), heparines, factor Xa inhibitors;
    b) platelet aggregation inhibitors (e.g. clopidrogrel, ticlopidine, prasugel, AZ4160);
4) modulators of lipid metabolism, for example,
    a) insulin sensitizers such as PPAR agonists (e.g. pioglitazone, rosiglitazone, Galida, muraglitazaar, gefemrozil, fenofibrate);
    b) HMG-CoA reductase inhibitors, statins (e.g. simvastatin, pravastatin, atorvaststin, rosuvastatin, fluvastatin, pitavastatin);
    c) cholesterol absorption inhibitors (e.g. ezetimibe);
    d) IBAT inhibitors (e.g. AZD-7806);
    e) LXR agonists (e.g. GW-683965A, T-0901317);
    f) PXR receptor modulators;
    g) phospholipase inhibitors;
5) anti-anginal agents, for example, nitrates and nitrites;
6) modulators of oxidative stress, for example, anti-oxidants. (probucol), myeloperoxidase inhibitors.

The invention is illustrated, but in no way limited, by the following examples:
General Methods All solvents used were analytical grade and commercially available anhydrous solvents were routinely used for reactions. Reactions were typically run under an inert atmosphere of nitrogen or argon.

$^1$H and $^{13}$C NMR spectra were recorded at 400 MHz for proton and 100 MHz for carbon-13 either on a Varian Unity+ 400 NMR Spectrometer equipped with a 5 mm BBO probe with Z-gradients, or a Bruker Avance 400 NMR spectrometer equipped with a 60 µl dual inverse flow probe with Z-gradients, or a Bruker DPX400 NMR spectrometer equipped with a 4-nucleus probe equipped with Z-gradients. 600 MHz $^1$H NMR spectra were recorded on a Bruker av600 NMR spectrometer equipped with a 5 mm BBI probehead with Z-gradients. 300 MHz $^1$H NMR spectra were recorded on a Varian Gemini 300 NMR equipped with a 5 mm BBI probehead. Unless specifically noted in the examples, spectra were recorded at 400 MHz for proton and 100 MHz for carbon-13. The following reference signals were used: the middle line of DMSO-$d_6$ δ 2.50 ($^1$H), δ 39.51 ($^{13}$C); the middle line of CD$_3$OD δ 3.31 ($^1$H) or δ 49.15 ($^{13}$C); acetone-$d_6$ 2.04 ($^1$H), 206.5 ($^{13}$C); and CDCl$_3$ δ 7.26 ($^1$H), the middle line of CDCl$_3$ δ 77.16 ($^{13}$C) (unless otherwise indicated). Enantiomeric excess was determined by GC on a Cyclodex B column (isothermic elution 100° C.).

Mass spectra were recorded on a Waters LCMS consisting of an Alliance 2795 (LC) and a ZQ single quadrupole mass spectrometer. The mass spectrometer was equipped with an electrospray ion source (ESI) operated in a positive or negative ion mode. The capillary voltage was 3 kV and the mass spectrometer was scanned from m/z 100-700 with a scan time of 0.3 or 0.8 s. Separations were performed on either Waters X-Terra MS, C8-columns, (3.5 µm, 50 or 100 mm×2.1 mm i.d.), or a ScantecLab's ACE 3 AQ column (100 mm×2.1 mm i.d.). The column temperature was set to 40° C. A linear gradient was applied using a neutral or acidic mobile phase system, running at 0% to 100% organic phase in 4-5 minutes, flow rate 0.3 ml/min. Neutral mobile phase system: acetonitrile/[10 mM NH$_4$OAc (aq.)/MeCN (95:5)], or [10 mM NH$_4$OAc (aq.)/MeCN (1/9)]/[10 mM NH$_4$OAc (aq.)/MeCN (9/1)]. Acidic mobile phase system: [133 mM HCOOH (aq.)/MeCN (5/95)]/[8 mM HCOOH (aq.)/MeCN (98/2)].

Alternatively, mass spectra were recorded on a GC-MS (GC 6890, 5973N MSD, Agilent Technologies) using a VF-5 MS column (ID 0.25 mm×30 m, 0.25 µm (Varian Inc.)). A linear temperature gradient was applied (40° C.-300° C.), 25° C./minute. The MS was equipped with a CI ion source and the reactant gas was methane. The MS was scanned between m/z 50-500 and the scan speed was set to 3.25 scan/s. HPLC analyses were performed on an Agilent HP1000 system consisting of G1379A Micro Vacuum Degasser, G1312A Binary Pump, G1367A Wellplate auto-sampler, G1316A Thermostatted Column Compartment and G1315B Diode Array Detector. Column: X-Terra MS, Waters, 4.6×50 mm, 3.5 µm. The column temperature was set to 40° C. and the flow rate to 1.5 m/min. The Diode Array Detector was scanned from 210-300 nm, step and peak width were set to 2 nm and 0.05 min, respectively. A linear gradient was applied, run from 0% to 100% acetonitrile, in 4 min. Mobile phase: acetonitrile/10 mM ammonium acetate in 5% acetonitrile in MilliQ Water.

A typical workup procedure after a reaction consisted of extraction of the product with a solvent such as ethyl acetate, washing with water followed by drying of the organic phase over MgSO$_4$ or Na$_2$SO$_4$, and concentration of the solution in vacuo.

Thin layer chromatography (TLC) was performed on Merck TLC-plates (Silica gel 60 F$_{254}$) and UV was used to visualize the spots. Flash chromatography was preformed on a Combi Flash® Companion™ using RediSep™ normal-phase flash columns or on Merck Silica gel 60 (0.040-0.063 mm). Typical solvents used for flash chromatography were mixtures of chloroform/methanol, toluene/ethyl acetate and ethyl acetate/hexanes. Preparative chromatography was run on a Gilson auto-preparative HPLC with a diode array detector. Column: XTerra MS C8, 19×300 mm, 7 µm. Gradient with acetonitrile/0.1M ammonium acetate in 5% acetonitrile in MilliQ Water, run from 20% to 60% acetonitrile, in 13 min. Flow rate: 20 ml/min. Alternatively, purification was achieved on a semi preparative Shimadzu LC-8A HPLC with a Shimadzu SPD-10A UV-vis.-detector equipped with a Waters Symmetry® column (C18, 5 µm, 100 mm×19 mm). Gradient with acetonitrile/0.1% trifluoroacetic acid in MilliQ Water, run from 35% to 60% acetonitrile in 20 min. Flow rate: 10 ml/min.

Recrystallization was typically performed in solvents or solvent mixtures such as ether, ethyl acetate/heptanes and methanol/water.

The following abbreviations have been used: DCM=dichloromethane; DIPCl=β-chlorodiisopinocamphenylborane (DIP-Chloride™); DIPEA=N,N-diisopropylethylamine; DMF=N,N-dimethylformamide; DMSO=dimethylsulfoxide; NCS=N-chlorosuccinimide; NMP=1-methyl-2-pyrrolidinone; THF=tetrahydrofuran; aq=aqueous; conc=concentrated.

Starting materials used were either available from commercial sources or prepared according to literature procedures and had experimental data in accordance to those reported. The following are examples of starting material that were prepared:
(1S)-1-(2-fluorophenyl)ethanol: Garrett, C. E. *Tetrahedron: Asymmetry* 2002, 13, 1347-1349; Doucet, H. *Chem. Eur. J.* 1999, 5, 1320-1330;
(R)—N-methylleucinol: Aitali, M.; Allaoud, S.; Karim, A.; Meliet, C.; Mortreux, A. *Tetrahedron: Asymmetry* 2000, 11, 1367-1374;
(2R)-2-[(2-amino-5-mercapto[1,3]thiazolo[4,5-d]pyrimidin-7-yl)amino]-4-methylpentan-1-ol: WO 02/076990;
5-(benzylthio)-7-chloro[1,3]thiazolo[4,5-d]pyrimidin-2-amine: WO 00/09511; 3-(1-hydroxyethyl)benzamide: Watson, C. Y; Whish, W. J. D; Threadgill, M. D. *Bioorg. Med. Chem.* 1998 6(6) 721-34;
1-[3-(methylsulfonyl)phenyl]ethanone: T. Fujita, J. Iwasa and C. Hansch, *Journal of the American Chemical Society* 1964, 86, 5175-5180;
(1-chloropropyl)benzene: Desai, V. R.; Nechvatal, A.; Tedder, J. M. *J. Chem. Soc.* (B) 1969, 30-32;
3-[(1S)-1-hydroxyethyl]benzonitrile: Belley, M. *Bioorg. Med. Chem.*, 1999, 7, 2697-2704;
1-(3-methoxyphenyl)ethanol: Handa, S. *J. Chem. Soc. Perkin Trans.* 1 1995, 1623-1633;
(2R)-2-amino-4-fluoro-4-methylpentan-1-ol: Truong, V. L; Gauthier, J. Y; Boyd, M; Roy, B; Scheigetz, J. *Synlett* 2005, 8, 1279-1280; following the route for the S enantiomer:
(1S)-1-(3-fluorophenyl)ethanol: Pastor, I. M. *Chem. Eur. J.* 2003, 9, 4031-4045.

General Method A

Sodium borohydride (0.1 equiv.), DIPEA (1.5 equiv.) and a compound of general formula (III) (1.2 equiv.) were added to a compound of general formula (II) (1.0 equiv.) in DMSO under a nitrogen atmosphere. The resulting reaction mixture was stirred at 40° C. until the reaction was complete (monitored by LC-MS, HPLC or TLC). The mixture was poured into ice water and the product was extracted with DCM or EtOAc. The combined organic phases were dried and concentrated in vacuo. The crude product was, if necessary, purified using preparative HPLC or by flash column chromatography.

General Method B

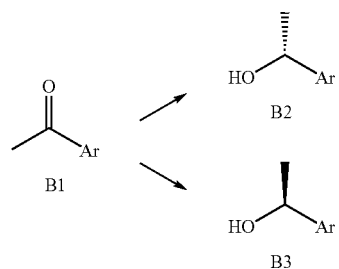

B1 (1.0 equiv.) in THF was added at 0° C. to (+)-DIPCl (to give B2) or (−)-DIPCl (to give B3) (1.5 equiv.) in THF under an argon atmosphere. The reaction mixture was allowed to slowly reach room temperature overnight. The solvent was evaporated off followed by the addition of Et₂O and diethanolamine (2.2 equiv.). The mixture was stirred until the reaction was complete (monitored by LC-MS, HPLC or TLC). The precipitate that formed was filtered off, washed with Et₂O and the filtrate was concentrated in vacuo. The crude product was, if necessary, purified using preparative HPLC or by flash column chromatography.

General Method C

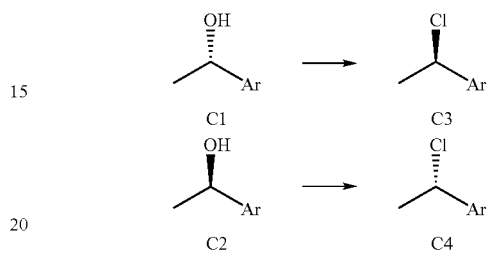

Triphenyl phosphine (1.3 equiv.) in THF was added at 0° C. to NCS (1.3 equiv.) in THF under an argon atmosphere. The resulting mixture was stirred at ambient temperature for 30 min. C1 or C2 (1 equiv.) was added at 0° C. and the reaction mixture was stirred at ambient temperature until the reaction was complete (monitored by LC-MS, HPLC or TLC). The solvent was evaporated off followed by addition of hexane and removal of the precipitate by filtration. The filtrate was concentrated in vacuo and the crude product was, if necessary, purified using preparative HPLC or by flash column chromatography.

EXAMPLE 1

(2R)-2-[(2-Amino-5-{[(1S)-1-(2-fluorophenyl)ethyl]thio}[1,3]thiazolo[4,5-d]pyrimidin-7-yl)amino]pentan-1-ol a) 1-[(1R)-1-Chloroethyl]-2-fluorobenzene The title compound was obtained in 65% yield with 93% enantiomeric excess using general method C starting from (1s)-1-(2-fluorophenyl)ethanol (3.56 g, 25 mmol).
¹H NMR (CDCl₃) δ 7.53 (td, 1H), 7.28 (m, 1H), 7.16 (m, 1H), 7.04 (m, 1H), 5.42 (q, 1H), 1.84 (d, 3H);
MS (ESI⁺) m/z 158 [M+H]⁺.

b) (2R)-2-{[2-Amino-5-(benzylthio)[1,3]thiazolo[4,5-d]pyrimidin-7-yl]amino}pentan-1-ol 5-(Benzylthio)-7-chloro[1,3]thiazolo[4,5-d]pyrimidin-2-amine (6.0 g, 19.4 mmol) was dissolved in NMP (30 mL). DIPEA (8.4 mL, 48.5 mmol) and 2-amino-(2R)-1-pentanol (3.5 g, 33.9 mmol) were added and the mixture was heated to 110° C. for 4 days. After cooling to ambient temperature, the mixture was poured into water (200 mL). The precipitated product was collected by filtration, washed with water and used in the next step without further purification (7.0 g, 97% yield).
MS (ESI⁺) m/z 376 [M+H]⁺.

c) (2R)-2-[(2-Amino-5-mercapto[1,3]thiazolo[4,5-d]pyrimidin-7-yl)amino]pentan-1-ol A round-bottomed flask was equipped with a dry ice-ethanol condenser and immersed in a dry ice-ethanol cooling bath. Ammonia (250 mL) was condensed into the flask followed by the addition of (2R)-2-{[2-amino-5-(benzylthio)[1,3]thiazolo[4,5-d]pyrimidin-7-yl]amino}pentan-1-ol (6.8 g, 18.1 mmol). The resulting mixture was allowed to warm to −33° C. and sodium metal was added in small pieces until a blue colour appeared and persisted for 30 seconds. The reaction was then quenched by addition of a spoon of solid ammonium chloride. The ammonia was evaporated off and water (250 mL) was added to the residue. The resulting mixture was neutralized with 1M HCl (aq.). The precipitated product was collected by filtration, washed with water and dried in vacuo to yield 4.15 g (80% yield) of the title compound.

MS (ESI$^+$) m/z 286 [M+H]$^+$.

d) (2R)-2-[(2-Amino-5-{[(1S)-1-(2-fluorophenyl)ethyl]thio}[1,3]thiazolo[4,5-d]pyrimidin-7-yl)amino]pentan-1-ol The title compound was obtained in 96% yield using general method A starting from (2R)-2-[(2-amino-5-mercapto[1,3]thiazolo[4,5-d]pyrimidin-7-yl)amino]pentan-1-ol (703 mg, 2.46 mmol) and 1-[(1R)-1-chloroethyl]-2-fluorobenzene (469 mg, 2.96 mmol).

$^1$H NMR (DMSO-d$_6$) δ 8.38 (br s, 2H), 7.55 (td, 1H), 7.32 (m, 1H), 7.20 (m, 1H), 7.18 (d, 1H), 5.26 (q, 1H), 4.19 (br s, 1H), 3.43 (dd, 5.6 Hz, 1H), 3.35 (dd, 1H), 1.69 (d, 3H), 1.66-1.42 (m, 2H), 1.39-1.21 (m, 2H), 0.86 (t, 3H);

MS (ESI$^+$) m/z 408 [M+H]$^+$.

EXAMPLE 2

(2R)-2-[(2-Amino-5-{[(1S)-1-(2-fluorophenyl)ethyl]thio}[1,3]thiazolo[4,5-d]pyrimidin-7-yl)amino]-4-methylpentan-1-ol The title compound was obtained in 41% yield using general method A starting from (2R)-2-[(2-amino-5-mercapto[1,3]thiazolo[4,5-d]pyrimidin-7-yl)amino]-4-methylpentan-1-ol (800 mg, 2.67 mmol), and 1-[(1R)-1-chloroethyl]-2-fluorobenzene (509 mg, 3.21 mmol).

$^1$H NMR (DMSO-d$_6$) δ 7.97 (s, 2H), 7.53 (td, 1H), 7.29 (m, 1H), 7.17 (m, 1H), 7.15 (d, 1H), 6.89 (d, 1H), 5.22 (q, 1H), 4.61 (t, 1H), 4.24 (br s, 1H), 3.38 (dt, 1H), 3.28 (m, 1H), 1.65 (d, 3H), 1.59 (m, 1H), 1.49-1.32 (m, 2H), 0.87 (d, 3H), 0.84 (d, 3H);

MS (ESI$^+$) m/z 422 [M+H]$^+$.

EXAMPLE 3

(2R)-2-({2-Amino-5-[(1-phenylethyl)thio][1,3]thiazolo[4,5-d]pyrimidin-7-yl}amino)-4-methylpentan-1-ol The title compound was obtained as a mixture of two diastereomers in 67% yield according to general method A starting from (2R)-2-[(2-amino-5-mercapto[1,3]thiazolo[4,5-d]pyrimidin-7-yl)amino]-4-methylpentan-1-ol (320 mg, 1.01 mmol) and (1-bromoethyl)-benzene (245 mg, 1.21 mmol).

$^1$H NMR (DMSO-d$_6$) δ 7.94 (s, 2H), 7.16 (m, 2H), 7.14 (m, 2H), 6.97 (m, 1H), 6.77 (d, 1H), 4.74 (m, 1H), 4.49 (m, 1H), 4.03 (m, 1H), 3.87 (m, 2H), 3.22 (m, 2H), 1.72 (dd, 1H), 1.61 (m, 1H), 1.42 (m, 2H), 0.87 (d, 3H), 0.85 (m, 3H);

MS (ES$^+$) m/z 405 [M+H]$^+$.

EXAMPLE 4

(2R)-2-[(2-Amino-5-{[(1R)-1-phenylethyl]thio}[1,3]thiazolo[4,5-d]pyrimidin-7-yl)amino]-4-methylpentan-1-ol HPLC purification of (2R)-2-({2-amino-5-[(1-phenylethyl)thio][1,3]thiazolo[4,5-d]pyrimidin-7-yl}amino)-4-methylpentan-1-ol (Example 3) (500 mg) provided the title single diastereomer (150 mg).

$^1$H NMR (DMSO-d$_6$) δ 7.98 (s, 2H), 7.45 (m, 2H), 7.32 (m, 2H), 7.24 (m, 1H), 6.87 (d, 1H), 4.95 (q, 1H), 4.24 (br s, 1H), 3.45 (m, 1H), 3.35 (m, 1H), 1.68 (d, 3H), 1.62 (m, 1H), 1.42 (m, 2H), 0.88 (d, 3H), 0.82 (d, 3H);

MS (ESI$^+$) m/z 405 [M+H]$^+$.

EXAMPLE 5

3-{(1S)-1-[(2-Amino-7-{[(1R)-1-(hydroxymethyl)butyl]amino}[1,3]thiazolo[4,5-d]pyrimidin-5-yl)thio]ethyl}benzonitrile a) 3-[(1R)-1-Chloroethyl]benzonitrile The title compound was obtained in 79% yield according to general method C starting from 3-[(1S)-1-hydroxyethyl]benzonitrile (3.35 g, 22.8 mmol).

$^1$H NMR (DMSO-d$_6$): δ 7.97 (s, 1H), 7.82 (m, 2H), 7.60 (t, 1H), 5.40 (q, 1H), 1.80 (d, 3H);

$^{13}$C NMR (DMSO-d$_6$): δ 144.1, 131.2, 131.6, 130.3, 129.9, 118.4, 111.6, 57.41, 25.5;

MS (ESI$^+$) m/z 166 [M+H]$^+$.

b) 3-{(1S)-1-[(2-Amino-7-{[(1R)-1-(hydroxymethyl)butyl]amino}[1,3]thiazolo[4,5-d]pyrimidin-5-yl)thio]ethyl}benzonitrile The title compound was obtained in 75% yield according to general method A starting from 2-amino-7-{[(1R)-1-(hydroxymethyl)butyl]amino}[1,3]thiazolo[4,5-d]pyrimidine-5(6H)-thione (2.87 g, 10.0 mmol) and 3-[(1R)-1-chloroethyl]benzonitrile (2.31 g, 13.9 mmol).

$^1$H NMR (DMSO-d$_6$): δ 8.00 (s, 2H), 7.91 (s, 1H), 7.82 (m, 1H), 7.69 (m, 1H), 7.52 (t, 1H), 6.90 (d, 1H), 5.00 (q, 1H), 4.63 (t, 1H), 4.13 (br s, 1H), 3.41 (m, 1H), 3.30 (m, 1H), 1.66 (d, 3H), 1.57 (m, 1H), 1.43 (m, 1H), 1.29 (m, 2H), 0.86 (t, 3H);

$^{13}$C NMR (DMSO-d$_6$): δ 170.8, 168.7, 165.1, 155.7, 145.9, 132.3, 130.8, 130.6, 129.5, 118.7, 111.2, 63.3, 59.7, 51.8, 42.3, 33.0, 21.8, 18.8, 14.0;

MS (ESI$^+$) m/z 415 [M+H]$^+$.

EXAMPLE 6

(2R)-2-{[2-Amino-5-({(1S)-1-[3-(methylsulfonyl)phenyl]ethyl}thio)[1,3]thiazolo[4,5-d]pyrimidin-7-yl]amino}-4-methylpentan-1-ol a) (1S)-1-[3-(Methylsulfonyl)phenyl]ethanol The title compound was prepared in 58% yield from 1-[3-(methylsulfonyl)phenyl]ethanone (2.00 g, 10.1 mmol) according to general method B.

MS (ESI$^+$) m/z 201 [M+H]$^+$.

b)
1-[(1R)-1-Chloroethyl]-3-(methylsulfonyl)benzene

The title compound was prepared in 21% yield from (1S)-1-[3-(methylsulfonyl)phenyl]ethanol (100 mg, 0.50 mmol) according to general method C.
MS (ESI$^+$) m/z 219 [M+H]$^+$.

c) (2R)-2-{[2-Amino-5-({(1S)-1-[3-(methylsulfonyl)phenyl]ethyl}thio)[1,3]thiazolo[4,5-d]pyrimidin-7-yl]amino}-4-methylpentan-1-ol The title compound was prepared from (2R)-2-[(2-amino-5-mercapto[1,3]thiazolo[4,5-d]pyrimidin-7-yl)amino]-4-methylpentan-1-ol (16.5 g, 55.3 mmol) and 1-[(1R)-1-chloroethyl]-3-(methylsulfonyl)benzene (12.1 g, 55.3 mmol) according to general method A.
$^1$H NMR (600 MHz, DMSO-d$_6$): δ 8.00 (m, 3H) 7.81 (m, 2H) 7.60 (t, 1H) 6.91 (d, 1H) 5.06 (q, 1H) 4.66 (t, 1H) 4.24 (br s, 1H) 3.38 (m, 1H) 3.28 (m, 1H) 3.23 (s, 3H) 1.69 (d, 3H) 1.59 (m, 1H) 1.34-1.46 (m, 2H) 0.86 (m, 6H);
MS (ESI$^+$) m/z 482 [M+H]$^+$.

EXAMPLE 7

(2R)-2-[(2-Amino-5-{[(1S)-1-phenylethyl]thio}[1,3]thiazolo[4,5-d]pyrimidin-7-yl)amino]pentan-1-ol a) [(1R)-1-Chloroethyl]benzene The title compound was obtained in 67% yield using general method C starting from (1S)-1-phenylethanol (25 g, 0.20 mol).
$^1$H NMR (CDCl$_3$) δ 7.42 (m, 2H), 7.36 (m, 2H), 7.30 (m, 1H), 5.09 (q, 1H), 1.85 (d, 3H);
MS (CI) m/z 141 [M+1]$^+$.

b) (2R)-2-[(2-Amino-5-{[(1S)-1-phenylethyl]thio}[1,3]thiazolo[4,5-d]pyrimidin-7-yl)amino]pentan-1-ol The title compound was obtained in 23% yield using general method A starting from (2R)-2-[(2-amino-5-mercapto[1,3]thiazolo[4,5-d]pyrimidin-7-yl)amino]pentan-1-ol (100 mg, 0.35 mmol) and [(1R)-1-chloroethyl]benzene (54 mg, 0.38 mmol).
$^1$H NMR (DMSO-d$_6$) δ ppm 7.96 (br s, 1H), 7.43 (d, 1H), 7.31 (m, 2H), 7.22 (m, 1H), 6.86 (d, 1H), 4.95 (m, 1H), 4.64 (t, 1H), 4.17 (br s, 1H), 3.44 (m, 1H), 3.35 (m, 1H), 1.66 (d, 3H), 1.58 (m, 1H), 1.44 (m, 1H), 1.36-1.21 (m, 2H), 0.85 (t, 3H);
MS (ESI$^+$) m/z 390 [M+H]$^+$.

EXAMPLE 8

3-{(1S)-1-[(2-Amino-7-{[(1R)-1-(hydroxymethyl)-3-methylbutyl]amino}[1,3]thiazolo[4,5-d]pyrimidin-5-yl)thio]ethyl}benzonitrile The title compound was prepared in 31% yield from (2R)-2-[(2-amino-5-mercapto[1,3]thiazolo[4,5-d]pyrimidin-7-yl)amino]-4-methylpentan-1-ol (200 mg, 0.67 mmol) and 3-[(1R)-1-chloroethyl]benzonitrile (166 mg, 1.0 mmol) according to general method A.
$^1$H NMR (CD$_3$OD) δ 7.89-7.76 (m, 2H) 7.57 (d, 1H) 7.49 (m, 1H) 5.12 (q, 1H) 4.42 (br s, 1H) 3.53 (m, 1H) 3.44 (m, 1H) 1.63-1.76 (m, 4H) 1.41-1.60 (m, 2H) 0.96 (t, 6H);
MS (ESI$^+$) m/z 429 [M+H]$^+$.

EXAMPLE 9

(2R)-2-({2-Amino-5-[(1-phenylpropyl)thio][1,3]thiazolo[4,5-d]pyrimidin-7-yl}amino)-4-methylpentan-1-ol The title compound was synthesized as a mixture of two diastereomers by general method A from the reaction of (2R)-2-[(2-amino-5-mercapto[1,3]thiazolo[4,5-d]pyrimidin-7-yl)amino]-4-methylpentan-1-ol (30 mg, 100 μmol) with (1-chloropropyl)benzene (15.5 μL, 100 μmol) to give 13 mg (31% yield) as an oil.
$^1$H NMR (CD$_3$OD) δ 7.39 (t, 2H) 7.28 (m, 2H) 7.20 (t, 1H) 4.85 (dd, 1H) 4.57-4.40 (m, 1H) 3.62 (m, 1H) 3.59-3.48 (m, 1H) 2.25-2.11 (m, 1H) 2.01 (m, 1H) 1.79-1.65 (m, 1H) 1.63-1.53 (m, 1H) 1.53-1.42 (m, 1H) 1.01-0.87 (m, 9H);
MS (ESI$^+$) m/z 418 [M+H]$^+$.

EXAMPLE 10

3-{(1R)-1-[(2-Amino-7-{[(1R)-1-(hydroxymethyl)-3-methylbutyl]amino}[1,3]thiazolo[4,5-d]pyrimidin-5-yl)thio]ethyl}benzamide a) 3-(1-Chloroethyl)benzamide Diethylaniline (390 μL, 2.45 mmol) was added 3-(1-hydroxyethyl)benzamide (400 mg, 2.45 mmol) slurried in DCM (20 mL) and the reaction mixture was cooled with an ice-bath. Thionyl chloride ((255 μL, 2.47 mmol) was added dropwise and the reaction was put in the refrigerator overnight. Water was added, the reaction mixture was extracted twice with DCM, washed with a 10% HCl solution, neutralized with a saturated bicarbonate solution, treated with brine, dried (MgSO$_4$), filtered and evaporated to dryness. The crude product was recrystallized from diethylether/hexane to give 335 mg (75% yield) of the title compound as a white solid.
$^1$H NMR (Chloroform-d) δ 7.90 (s, 1H) 7.73 (d, 1H) 7.62 (d, 1H) 7.46 (t, 1H) 5.14 (q, 1H) 1.88 (d, 3H) 1.60 (s, 2H);
MS (ESI$^+$) m/z 183, 185 [M+H]$^+$.

b) 3-{(1R)-1-[(2-Amino-7-{[(1R)-1-(hydroxymethyl)-3-methylbutyl]amino}[1,3]thiazolo[4,5-d]pyrimidin-5-yl)thio]ethyl}benzamide The title compound was synthesized as a mixture of two diastereomers by general method A from the reaction of (2R)-2-[(2-amino-5-mercapto[1,3]thiazolo[4,5-d]pyrimidin-7-yl)amino]-4-methylpentan-1-ol (30 mg, 100 μmol) with 3-(1-chloroethyl)benzamide (20 mg, 100 μmol). Separation of the mixture by preparative HPLC gave a single diastereomer (6 mg, 13% yield) as an oil.
$^1$H NMR (CD$_3$OD) δ 7.99 (s, 1H) 7.73 (d, 1H) 7.69 (d, 1H) 7.41 (t, 1H) 5.15 (q, 1H) 4.43-4.52 (m, 1H) 3.54 (m, 1H) 3.47 (m, 1H) 1.74 (d, 3H) 1.70 (m, 1H) 1.59-1.42 (m, 2H) 0.96 (t, 6H);
MS (ESI$^+$) m/z 447 [M+H]$^+$.

EXAMPLE 11

(2R)-2-{[2-Amino-5-({1-[3-(trifluoromethyl)phenyl]ethyl}thio)[1,3]thiazolo[4,5-d]pyrimidin-7-yl]amino}-4-methylpentan-1-ol The title compound was synthesized as a mixture of two diastereomers by general method A from the reaction of (2R)-2-[(2-amino-5-mercapto[1,3]thiazolo[4,5-d]pyrimidin-7-yl)amino]-4-methylpentan-1-ol (30 mg, 0.1 mmol) with 3-(1-bromoethyl)trifluoromethylbenzene (15.5 μL, 0.1 mmol) to give 38 mg (81% yield) as an oil.

$^1$H NMR (600 MHz, CD$_3$OD) δ 7.81-7.71 (m, 2H) 7.57-7.44 (m, 2H) 5.16 (q, 1H) 4.43 (s, 0.5H) 4.31 (s, 0.5H) 3.59 (m, 1H) 3.55-3.40 (m, 1H) 1.74 (t, 3H) 1.69 (m, 0.5H) 1.63 (m, 0.5H) 1.54 (m, 1H) 1.49-1.37 (m, 1H) 0.96 (dd, 3H) 0.86 (dd, 1.5H);

MS (ESI$^+$) m/z 472 [M+H]$^+$.

EXAMPLE 12

(2R)-2-[{2-Amino-5-[(1-phenylethyl)thio][1,3]thiazolo[4,5-d]pyrimidin-7-yl}(methyl)amino]-4-methylpentan-1-ol a) (2R)-2-[[2-Amino-5-(benzylthio)[1,3]thiazolo[4,5-d]pyrimidin-7-yl](methyl)amino]-4-methylpentan-1-ol 5-(Benzylthio)-7-chloro[1,3]thiazolo[4,5-d]pyrimidin-2-amine (1.5 g, 4.86 mmol), DIPEA (691 mg, 5.35 mmol) and (R)—N-methylleucinol (956 mg, 7.29 mmol) were mixed in NMP (7.5 mL). The resulting solution was stirred at 110° C. under a nitrogen atmosphere for 2 days. After cooling to room temperature the reaction mixture was poured onto ice. The resulting yellow precipitate was collected by filtration, washed with water and dried in vacuo. The crude product was purified by flash column chromatography on silica (DCM: EtOAc 50:50 to 0:100) to give 1.42 g (72% yield) of the title compound as a yellow solid.

$^1$H NMR (DMSO-d$_6$) δ 7.97 (br s, 2H), 7.40 (m, 2H), 7.28 (m, 2H), 7.21 (m, 1H), 4.73 (dd, 1H), 4.64 (br s, 1H), 4.32 (br s, 2H), 3.52-3.37 (m, 2H), 3.00 (s, 3H), 1.55-1.35 (m, 2H), 1.27 (m, 1H), 0.88 (d, 3H), 0.80 (d, 3H);

MS (ESI$^+$) m/z 404 [M+H]$^+$.

b) (2R)-2-[(2-Amino-5-mercapto[1,3]thiazolo[4,5-d]pyrimidin-7-yl)(methyl)amino]-4-methylpentan-1-ol A three-neck round-bottomed flask was immersed in a dry ice/ethanol cooling bath and equipped with a dry ice/ethanol condenser. The system was flushed with nitrogen and ammonia (approximately 50 mL) was condensed into the flask. (2R)-2-[[2-Amino-5-(benzylthio)[1,3]thiazolo[4,5-d]pyrimidin-7-yl](methyl)amino]-4-methylpentan-1-ol (1 g, 2.5 mmol) was added to the flask, resulting in a clear yellow solution. Small pieces of sodium metal (size 2-3 mm) were added one by one to the reaction mixture. When a persistent blue colour (>20 sec) appeared, a spoon of solid NH$_4$Cl was added to quench the reaction. The ammonia was evaporated off. Water (50 mL) was added and the mixture was neutralized with 1M HCl (aq.) to pH 7. The precipitated yellow solid was collected by filtration, washed with water and dried in vacuo to yield 630 mg of the title compound (80% yield).

$^1$H NMR (DMSO-d$_6$) δ 12.78 (br s, 1H), 8.43 (br s, 2H), 4.84 (br, 2H), 3.52-3.38 (m, 2H), 3.01 (s, 3H), 1.55-1.33 (m, 2H), 1.32-1.20 (m, 1H), 0.87 (m, 6H);

MS (ESI$^+$) m/z 314 [M+H]$^+$.

c) (2R)-2-[{2-Amino-5-[(1-phenylethyl)thio][1,3]thiazolo[4,5-d]pyrimidin-7-yl}(methyl)amino]-4-methylpentan-1-ol The title compound was synthesized as a mixture of two diastereomers by general method A from the reaction of (2R)-2-[(2-amino-5-mercapto[1,3]thiazolo[4,5-d]pyrimidin-7-yl)(methyl)amino]-4-methylpentan-1-ol (31.4 mg, 0.1 mmol) with 1-bromoethylbenzene (13.5 μL, 0.1 mmol) to give 26 mg (62% yield).

$^1$H NMR (DMSO-d$_6$) δ 7.96 (s, 2H) 7.43 (t, 2H) 7.32 (m, 2H) 7.23 (t, 1H) 5.02-4.92 (m, 1H) 4.83-4.71 (m, 1H) 4.64 (s, 1H) 3.53-3.38 (m, 2H) 3.01 (d, 3H) 1.68 (dd, 3H) 1.52 (m, 1H) 1.43 (m, 1H) 1.35-1.24 (m, 1H) 0.88 (d, 3H) 0.83 (d, 3H);

MS (ESI$^+$) m/z 418 [M+H]$^+$.

EXAMPLE 13

(2R)-2-[(2-Amino-5-{[1-(2-chlorophenyl)ethyl]thio}[1,3]thiazolo[4,5-d]pyrimidin-7-yl)amino]-4-methylpentan-1-ol a) 1-Chloro-2-(1-chloroethyl)benzene Thionyl chloride (1.49 g, 12.6 mmol) was added to 1-(2-chlorophenyl)ethanol (1.0 g, 6.3 mmol) in toluene (50 mL) and the mixture was allowed to stir at room temperature for 2 h. To the reaction mixture was added 10% aq. HCl solution (20 mL). The organic phase was separated and washed with another portion of 10% aq. HCl solution, brine (20 mL) and then separated, dried and evaporated to provide 1-chloro-2-(1-chloroethyl)benzene in 72% yield.

$^1$H NMR (DMSO-d$_6$) δ 7.72 (1H, d), 7.48 (1H, m), 7.39 (2H, m), 5.59 (1H, q), 1.84 (3H, d).

b) (2R)-2-[(2-Amino-5-{[1-(2-chlorophenyl)ethyl]thio}[1,3]thiazolo[4,5-d]pyrimidin-7-yl)amino]-4-methylpentan-1-ol The title compound was obtained as a mixture of two diastereomers in 24% yield according to general method A starting from (2R)-2-[(2-amino-5-mercapto[1,3]thiazolo[4,5-d]pyrimidin-7-yl)amino]-4-methylpentan-1-ol (20 mg, 0.047 mmol) and 1-chloro-2-(1-chloroethyl)benzene (10 mg, 0.057 mmol).

$^1$H NMR (DMSO-d$_6$) δ 7.83 (2H, m), 7.48 (1H, d), 7.32 (1H, m), 7.15 (1H, m), 7.14 (1H, m), 6.79 (1H, d), 5.22 (1H, m), 4.13 (1H, m), 3.29-3.17 (2H, m), 1.52 (3H, dd), 1.47 (1H, m), 1.31 (1H, m), 1.25 (1H, m), 0.76 (3H, dd), 0.73 (3H, dd);

$^{13}$C NMR (DMSO-d$_6$) δ 171.18, 169.14, 165.75, 165.64, 155.97, 140.63, 132.62, 129.91, 129.04, 128.96, 127.94, 64.08, 63.88, 50.59, 24.70, 23.67, 22.33, 22.22, 22.01;

MS (ESI$^+$) m/z 438, 440 [M+H]$^+$.

EXAMPLE 14

(2R)-2-[(2-Amino-5-{[1-(3-methoxyphenyl)ethyl]thio}[1,3]thiazolo[4,5-d]pyrimidin-7-yl)amino]-4-methylpentan-1-ol a) 1-(1-Chloroethyl)-3-methoxybenzene The title compound was obtained in 59% yield starting from 1-(3-methoxyphenyl)ethanol (0.5 g, 3 mmol) and using the method of Example 13 (a).

$^1$H NMR (CDCl$_3$) δ 7.22 (1H, m), 6.76 (2H, m), 6.62 (1H, dd), 4.81 (1H, q), 3.57 (3H, s), 1.62 (3H, d).

b) (2R)-2-[(2-Amino-5-{[1-(3-methoxyphenyl)ethyl]thio}[1,3]thiazolo[4,5-d]pyrimidin-7-yl)amino]-4-methylpentan-1-ol The title compound was obtained as a mixture of two diastereomers in 25% yield according to general method A starting from (2R)-2-[(2-amino-5-mercapto[1,3]thiazolo[4,5-d]pyrimidin-7-yl)amino]-4-methylpentan-1-ol (20 mg, 0.07 mmol) and 1-(1-chloroethyl)-3-methoxybenzene (9.7 mg, 0.06 mmol).

$^1$H NMR (DMSO-$d_6$) δ 7.89 (2H, s), 7.13 (1H, m), 6.87 (2H, m), 6.80 (1H, m), 6.71 (1H, m), 4.86 (1H, m), 4.55 (1H, br s), 4.17 (1H, m), 3.64 (3H, s), 1.51 (3H, d), 1.48 (1H, m), 1.31 (2H, m), 0.76 (6H, m);

MS (ESI$^+$) m/z 434 [M+H]$^+$.

EXAMPLE 15

(2R)-2-[(2-amino-5-{[(1S)-1-phenylethyl]thio}[1,3]thiazolo[4,5-d]pyrimidin-7-yl)amino]-4-methylpentan-1-ol i) Using Process (a)

(2R)-2-[(2-Amino-5-{[(1S)-1-phenylethyl]thio}[1,3]thiazolo[4,5-d]pyrimidin-7-yl)amino]-4-methylpentan-1-ol The title compound was obtained in 42% yield using general method A starting from (2R)-2-[(2-amino-5-mercapto[1,3]thiazolo[4,5-d]pyrimidin-7-yl)amino]-4-methylpentan-1-ol (27 g, 90 mmol) and [(1R)-1-chloroethyl]benzene (19 g, 135 mmol).

$^1$H NMR (DMSO-$d_6$) δ 7.95 (br s, 2H), 7.43 (m, 2H), 7.31 (m, 2H), 7.22 (m, 1H), 6.85 (d, 1H), 4.96 (q, 1H), 4.64 (t, 1H), 4.27 (br s, 1H), 3.44-3.30 (m, 2H), 1.66 (d, 3H), 1.59 (m, 1H), 1.41 (m, 2H), 0.87 (d, 3H), 0.84 (d, 3H);

MS (ESI$^+$) m/z 404 [M+H]$^+$.

ii) Using Process (b)

a) 6-Amino-2-{[(1S)-1-phenylethyl]thio}pyrimidin-4-ol

NaH (60% in oil) (0.5 g, 12.5 mmol) followed by NaBH$_4$ (40 mg, 1 mmol) was added to 6-amino-2-mercaptopyrimidin-4-ol monohydrate (1.6 g, 10 mmol) in DMF (20 mL). After 30 min, [(1R)-1-chloroethyl]benzene (1.4 g, 10 mmol) was added and the reaction mixture was stirred for 16 h. The reaction was concentrated in vacuo to ca. 10 mL volume and then poured into water (ca. 50 mL). The precipitated solid material was filtered off and washed with water and ether to give the title compound (1.15 g, 46% yield).

$^1$H NMR (DMSO-$d_6$) δ 7.46-7.22 (m, 5H), 6.53 (br s, 2H), 4.99 (q, 1H), 4.92 (s, 1H), 1.67 (d, 3H).

b) 2-Amino-5-{[(1S)-1-phenylethyl]thio}[1,3]thiazolo[4,5-d]pyrimidin-7-ol

Pyridine (0.6 g, 7.6 mmol) was added to 6-amino-2-{[(1S)-1-phenylethyl]thio}pyrimidin-4-ol (1 g, 4 mmol) and KSCN (1.7 g, 16 mmol) in DMF (20 mL). The reaction mixture was cooled to 0° C. and bromine (0.65 g, 4.0 mmol) was then added in one portion. The reaction mixture was poured into water after 2 h and the orange precipitate was filtered off and washed with water. The solid was suspended in a mixture of DMF (6 mL) and water (2 mL) and heated to 110° C. After 30 h, the reaction mixture was poured into water, the yellowish precipitate was filtered off and washed with water and ether. The solid was dried in vacuum at 40° C. to give the title compound (0.8 g, 65% yield).

$^1$H NMR (DMSO-$d_6$) δ 8.16 (br s, 1H), 7.47-7.24 (m, 5H), 5.05 (q, 1H), 1.71 (d, 3H).

c) 7-Chloro-5-{[(1S)-1-phenylethyl]thio}[1,3]thiazolo[4,5-d]pyrimidin-2-amine POCl$_3$ (1 mL) was added to DMF (1 mL) in dioxane (6 mL). 2-Amino-5-{[(1S)-1-phenylethyl]thio}[1,3]thiazolo[4,5-d]pyrimidin-7-ol (1 g, 3.3 mmol) was added to the reaction in one portion. POCl$_3$ (1 mL) was added and the reaction mixture was heated to 80° C. for about 30 min. The reaction was cooled to room temperature and poured onto ice. The resulting mixture was heated at reflux for about 5 h. The mixture was allowed to attain room temperature and was then extracted with EtOAc. The organic layer was passed through a layer of silica gel and concentrated to dryness to give the title compound (1 g, 95% yield).

1H NMR (DMSO-$d_6$) δ 8.91 (br s, 2H), 7.47-7.20 (m, 5H), 4.95 (q, 1H), 1.69 (d, 3H).

d) 2R)-2-[(2-amino-5-{[(1S)-1-phenylethyl]thio}[1,3]thiazolo[4,5-d]pyrimidin-7-yl)amino]-4-methylpentan-1-ol DIPEA (400 mg, 3 mmol) and D-leucinol (400 mg, 3.4 mmol) were added to 7-chloro-5-{[(1S)-1-phenylethyl]thio}[1,3]thiazolo[4,5-d]pyrimidin-2-amine (300 mg, 0.9 mmol) in NMP (6 mL) and the mixture was heated to 120° C. for 24 h. The mixture was poured into water and extracted with ethyl acetate. The organic phase was dried (MgSO$_4$), evaporated and the residue was purified by flash column chromatography (EtOAc) to give the title compound (200 mg, 54% yield).

$^1$H NMR (DMSO-$d_6$) δ 7.95 (br s, 2H), 7.43 (m, 2H), 7.31 (m, 2H), 7.22 (m, 1H), 6.85 (d, 1H), 4.96 (q, 1H), 4.64 (t, 1H), 4.27 (br s, 1H), 3.44-3.30 (m, 2H), 1.66 (d, 3H), 1.59 (m, 1H), 1.41 (m, 2H), 0.87 (d, 3H), 0.84 (d, 3H);

MS (ESI$^+$) m/z 404 [M+H]$^+$.

EXAMPLE 16

(2R)-2-[(2-amino-5-{[(1S)-1-phenylethyl]thio}[1,3]thiazolo[4,5-d]pyrimidin-7-yl)amino]-4-fluoro-4-methylpentan-1-ol DIPEA (0.83 mL, 4.75 mmol) was added to a solution of 7-chloro-5-{[(1S)-1-phenylethyl]thio}[1,3]thiazolo[4,5-d]pyrimidin-2-amine (0.49 g, 1.52 mmol) and (2R)-2-amino-4-fluoro-4-methylpentan-1-ol (2 mmol) in NMP (2 mL) and the reaction mixture was stirred at 120° C. for 22 h. HPLC purification provided the title compound (0.22 g, 17% yield).

$^1$H NMR (400 MHz, CD$_3$OD): δ 7.48 (m, 2H), 7.32 (m, 2H), 7.23 (m, 1H), 5.09 (q, 1H), 4.66 (br s, 1H), 3.61-3.47 (m, 2H), 2.12-1.89 (m, 2H), 1.75 (d, 3H), 1.40 (m, 6H);

MS (ESI$^+$) m/z 422 [M+H]$^+$.

EXAMPLE 17

(2R)-2-[(2-amino-5-{[(1S)-1-(2-fluorophenyl)ethyl]thio}[1,3]thiazolo[4,5-d]pyrimidin-7-yl)amino]-4-fluoro-4-methylpentan-1-ol a) 6-Amino-2-{[(1S)-1-(2-fluorophenyl)ethyl]thio}pyrimidin-4-ol

NaH (60% in oil, 1.05 g, 26.3 mmol) was added in portions followed by NaBH$_4$ (0.099 g, 2.7 mmol) to 6-amino-2-mercaptopyrimidin-4-ol monohydrate (4.23 g, 26.3 mmol) in DMF (40 mL). After 30 minutes, 1-[(1R)-1-chloroethyl]-2-fluorobenzene (5.0 g, 31.5 mmol) in DMF (10 mL) was added and the reaction mixture was stirred for 24 h. The reaction mixture was concentrated and partitioned between water and DCM, the organic phase was dried (MgSO$_4$) and evaporated. The residue was purified by flash column chromatography (a stepwise gradient of 5-10% MeOH in CHCl$_3$) to give the title compound (5.20 g, 75% yield).

$^1$H NMR (400 MHz, DMSO-d$_6$): δ 7.35 (m, 1H), 7.13 (m, 1H), 6.99 (m, 2H), 6.29 (s, 2H), 5.00 (q, 1H), 4.76 (br s, 1H), 1.49 (d, 3H);

MS (ESI$^+$) m/z 266 [M+H]$^+$.

b) 2-Amino-5-{[(1S)-1-(2-fluorophenyl)ethyl]thio}[1,3]thiazolo[4,5-d]pyrimidin-7-ol KSCN (10.76 g, 110.7 mmol) and pyridine (3.9 mL, 49.2 mmol) was added to 6-amino-2-{[(1S)-1-(2-fluorophenyl)ethyl]thio}pyrimidin-4-ol (6.53 g, 24.6 mmol) in DMF (70 mL). The mixture was cooled to 0° C. and Br$_2$ was added dropwise. After 3.5 h the reaction mixture was poured into water and the formed precipitate was collected by filtration. The solid was suspended in a mixture of DMF (75 mL) and water (15 mL) and heated to 120° C. for 8 h. The reaction mixture was poured into water and the solid was collected by filtration and dried in vacuum at 40° C. to give the title compound (6.42 g, 81% yield).

MS (ESI$^+$) m/z 323 [M+H]$^+$.

c) 7-Chloro-5-{[(1S)-1-(2-fluorophenyl)ethyl]thio}[1,3]thiazolo[4,5-d]pyrimidin-2-amine POCl$_3$ (2.77 mL, 29.7 mmol) was added to DMF (3.07 mL, 39.6 mmol) in dioxane (30 mL). After 30 minutes this mixture was added to a solution of 2-amino-5-{[(1S)-1-(2-fluorophenyl)ethyl]thio}[1,3]thiazolo[4,5-d]pyrimidin-7-ol (6.38 g, 19.8 mmol) in dioxane (100 mL). After 30 minutes POCl$_3$ (2.77 mL, 29.7 mmol) was added, the reaction mixture was heated to 80° C. for 2 h. After cooling to room temperature, water (20 mL) was carefully added and the resulting mixture was stirred at 80° C. for 30 minutes and at room temperature for 2 h. The reaction mixture was poured into water and the formed precipitate was collected. The solid was purified by flash column chromatography (5% MeOH in CHCl$_3$) to give the title compound (5.91 g, 88% yield).

$^1$H NMR (400 MHz, DMSO-d$_6$): δ 8.94 (s, 2H), 7.58 (m, 1H), 7.32 (m, 1H), 7.20 (m, 2H), 5.22 (q, 1H), 1.71 (d, 3H);

MS (ESI$^+$) m/z 341 [M+H]$^+$.

d) (2R)-2-[(2-Amino-5-{[(1S)-1-(2-fluorophenyl)ethyl]thio}[1,3]thiazolo[4,5-d]pyrimidin-7-yl)amino]-4-fluoro-4-methylpentan-1-ol DIPEA (2.09 mL, 12.0 mmol) was added to 7-chloro-5-{[(1S) -1-(2-fluorophenyl)ethyl]thio}[1,3]thiazolo[4,5-d]pyrimidin-2-amine (1.36 g, 4.0 mmol) and (2R)-2-amino-4-fluoro-4-methylpentan-1-ol (4 mmol) in NMP (3 mL). After stirring the reaction mixture at 120° C. for 22 h it was poured into water and the precipitate was collected by filtration. The solid was purified by flash column chromatography (a stepwise gradient of 5%-10% MeOH in CHCl$_3$) and preparative HPLC to give the title compound (0.22 g, 13% yield).

$^1$H NMR (400 MHz, CD$_3$OD): δ 7.35 (m, 1H), 7.03 (m, 1H), 6.91 (m, 2H), 5.15 (q, 1H), 4.40 (m, 1H), 3.35-3.21 (m, 2H), 1.82-1.72 (m, 2H), 1.50 (d, 3H), 1.17 (m, 6H);

MS (ESI$^+$) m/z 440 [M+H]$^+$.

EXAMPLE 18

(2R)-2-[(2-Amino-5-{[(1S)-1-(3-fluorophenyl)ethyl]thio}[1,3]thiazolo[4,5-d]pyrimidin-7-yl)amino]-4-methylpentan-1-ol a) 1-[(1R)-1-Chloroethyl]-3-fluorobenzene The title compound was obtained in 49% yield with 94.5% enantiomeric excess using general method C starting from (1S)-1-(3-fluorophenyl)ethanol (4.20 g, 30 mmol).

$^1$H NMR (300 MHz, DMSO-d$_6$) δ 7.47-7.30 (m, 3H); 7.16 (t, 1H); 5.36 (q, 1H); 1.78 (d, 3H).

b) (2R)-2-[(2-Amino-5-{[(1S)-1-(3-fluorophenyl)ethyl]thio}[1,3]thiazolo[4,5-d]pyrimidin-7-yl)amino]-4-methylpentan-1-ol The title compound was obtained in 61% yield using general method A starting from (2R)-2-[(2-amino-5-mercapto[1,3]thiazolo[4,5-d]pyrimidin-7-yl)amino]-4-methylpentan-1-ol (0.30 g, 1.0 mmol), 1-[(1R)-1-chloroethyl]-3-fluorobenzene (0.17 g, 1.1 mmol) and NaBH$_4$ (0.019 g, 0.5 mmol).

$^1$H NMR (400 MHz, CD$_3$OD): δ 7.23 (m, 2H), 7.13 (m, 1H), 6.86 (m, 1H), 5.01 (q, 1H), 4.38 (m, 1H), 3.43 (m, 2H), 1.63 (d, 3H), 1.44 (m, 2H), 0.88 (m, 6H);

MS (ESI$^+$) m/z 422 [M+H]$^+$.

Pharmacological Screens

Materials

Recombinant human fractalkine (hCX$_3$CL1) and recombinant human interleukin-8 (IL-8 or hCXCL8) were purchased from PeproTech Inc., UK. Recombinant [$^{125}$I]-fractalkine (human) and [$^{125}$I] hIL-8 with the specific activity of 2200 Ci/mmol, was purchased from NEN® Life Science Products, Inc., UK. Fluo4-AM was purchased from Molecular Probes, US. All other chemicals were of analytical grade.

Cells

The complete human CX3CR1 cDNA (GenBank accession number U20350) was extracted from human brain mRNA (Superscript, Life Technologies) and ligated into pCR-Blunt II TOPO vector (InVitrogen). The insert corresponding hCX3CR1 was isolated and further subcloned into pcDNA3.1zeo. Plasmid DNA was prepared using Plasmid Midi Kit (Qiagen). Using Superfect Transfection Reagent (Qiagen) according to the manufacturer's protocol the expression plasmid for hCX$_3$CR1 was then introduced into human embryonic kidney suspension (HEKS) 293 cell line containing a vector for stable expression of a chimeric G-protein Gα$_{qi5}$. A stable clone was generated utilizing zeocin (500 μg/mL) and hygromycin (100 μg/mL) selection. For further applications the cells were maintained in Dulbecco's modified Eagle's medium/Ham's nutrient mix F12 (DMEM/F12) containing pyridoxine and supplemented with 10% (v/v) fetal bovine serum, 2 mM L-glutamine, 100 U/ml penicillin and 100 mg/ml streptomycin, 250 μg/mL zeocin and 100 μg/mL hygromycin.

Cells expressing human CXCR2 obtained from AstraZeneca Charnwood are cultured in EMEM containing Glutamax and supplemented with 10% FBS (from PAA, Austria), 1% non-essential amino acids (NEAA), 100 U/mL penicillin and 100 μg/mL streptomycin (PEST) and 500 μg/mL geneticin/G418.

Membrane Preparation

Cells are grown at 37° C. and 5% $CO_2$ and harvested at 60-80% confluence in buffer containing 10 mM Tris-HCl pH 7.4, 5 mM EDTA, 0.1 mg/mL bacitracin. The cells are centrifuged at 300×g for 10 min and the pellet is resuspended in harvesting buffer (10 mM Tris-HCl, pH 7.4, 5 mM ethylenediaminetetra-aceticacid (EDTA) and 0.1 mg/mL bacitracin), pooled and homogenised using a Dounce homogeniser. The homogenate is centrifuged in 48000×g for 10 min and resuspended in harvesting buffer using Ultra-Turrax T8. Membrane aliquots are stored at −80° C. Protein concentration was determined in microtiter plates as described by Harrington (1990, Anal. Biochem. 186, 285-287).

In Vitro Receptor Binding Assay

Competition binding studies of [$^{125}$I]fraktalkine were performed in 2 mL 96-deep-well plates (Beckman, Germany) in a total volume of 1000 μL/well. Each well contained 10 pM [$^{125}$I]-fractalkine and membrane equivalent to receptor concentration of 1 pM in assay buffer (50 mM Hepes-KOH, pH 7.4, 10 mM $MgCl_2$, 1 mM EDTA, 0.1% (w/v) gelatine). Ten concentrations (2 points/log unit) of the test compounds were pre-dissolved in DMSO and added to reach a final concentration of 1% (v/v) DMSO. The assay was initiated with the addition of membranes and incubated at 25° C. for 24 h. The reactions were stopped by rapid filtration through Whatman GF/B glass fiber filters pretreated with 0.3% polyethylimine and subsequent washing with ice-cold buffer (10 mM Hepes-KOH pH 7.4, 500 mM NaCl) using a Brandel receptor binding harvester. Scintillation cocktail was added and radioactivity was determined in a Packard 2500TR liquid scintillation counter. (Perkin Elmer, USA)

The [$^{125}$I]-hIL-8 competition binding studies are performed in singlicates in white clear bottom 96-well isoplates with a final volume of 200 μL and each well contains 150 pM [$^{125}$I]-hIL-8 (specific activity 2200 Ci/mmol), membrane-SPA preparation equivalent to 20 pM receptors and 1.5 mg SPA-beads in assay buffer [50 mM HEPES-KOH pH 7.4, 10 mM $MgCl_2$, 1 mM EDTA, 0.5% (w/v) gelatin]. The test compounds were treated as above. The non-specific binding is determined in the presence of 500 nM unlabelled hIL-8. The agonist hIL-8 (a concentration-response curve from 3 pM to 30 nM), is used as reference compound at each test occasion. The peptide curve does not contain DMSO. The binding reaction is started by addition of 140 μL membrane-SPA preparation, and the samples are incubated in dark at RT for 4 h. Assay plates are counted in a liquid scintillation counter (Wallac MicroBeta® TriLux 1450 from PerkinElmer, USA).

[$^{35}$S]GTPγS Binding

The [$^{35}$S]GTPγS binding studies were carried out in clear-bottom microtiter plates in duplicates with 10 concentrations of the inhibitor (2 conc/log units) diluted in DMSO (final conc 1%) and at room temperature. Membranes expressing the hCX3CR1 receptor (final concentration 20 μg protein/well) were added together with SPA beads (final concentration 1 mg/well) all suspended in GTPγS binding buffer (50 mM Tris-HCl, 100 mM NaCl, 0.1% gelatin, 15 μg saponin/mL and 3 μM GDP, pH 7.4 at rt). Membranes, SPA beads and drugs were pre-incubated 30 min before addition of 310 pM fraktalkine for maximal stimulation. Basal activity was defined as the activity found without fraktalkine stimulation (GTPγS binding buffer). After additional 30 min the reaction was started with the addition of [$^{35}$S]GTPγS to a final concentration of 0.1 nM and a final assay volume of 0.2 mL. The experiment was terminated 30 minutes later by centrifugation at 2000 rpm for 2×5 minutes (different directions) and the radioactivity determined in a liquid scintillation counter (Wallac MicroBeta® TriLux 1450).

Results

Receptor binding data for selected compounds of the present invention are shown in Table 1. Corresponding data for reference compounds are shown in Table 2.

Comparison of the data in Tables 1 and 2 shows clearly that the compounds of the present invention wherein $R^1$ represents Me or Et are both more potent antagonists at the $CX_3CR1$ receptor and less potent antagonists at the CXCR2 receptor than corresponding reference compounds wherein $R^1$ represents H. Such enhanced selectivity with respect to antagonism of the CX3CR1 receptor is expected to result in significant therapeutic benefit.

TABLE 1

| Compound | $K_i$ nM | |
|---|---|---|
| | $CX_3CR1$ | CXCR2 |
| 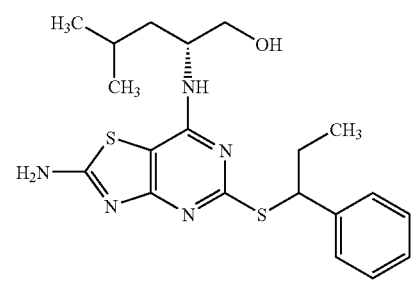 Example 9 | 3.1 | 2765 |
| 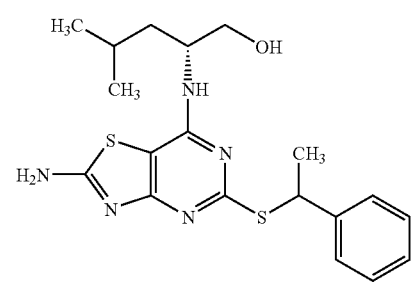 Example 3 | 3.8 | 3428 |
| 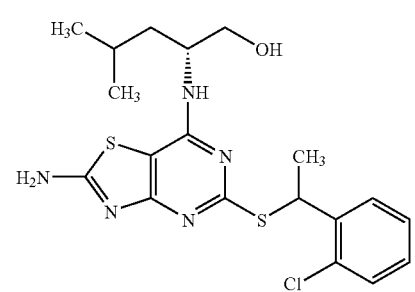 Example 13 | 5.9 | 5655 |

TABLE 1-continued

| Compound | K_i nM | |
|---|---|---|
| | CX_3CR1 | CXCR2 |
| 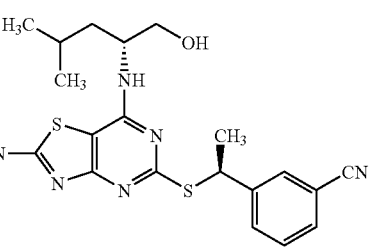 Example 8 | 14 | 4210 |
| 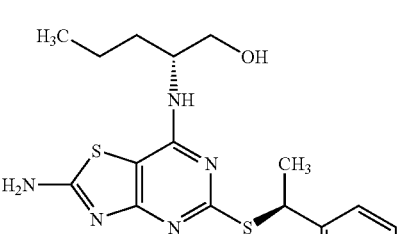 Example 7 | 52 | 1143 |

TABLE 2

| Compound | K_i nM | |
|---|---|---|
| | CX_3CR1 | CXCR2 |
| 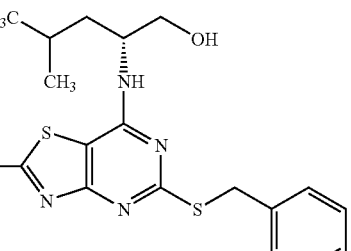 WO 00/09511 Example 70 | 48 | 531 |
| 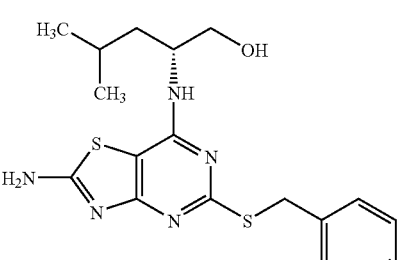 WO 02/076990, Example 6 | 51 | 1809 |

TABLE 2-continued

| Compound | K_i nM | |
|---|---|---|
| | CX_3CR1 | CXCR2 |
| 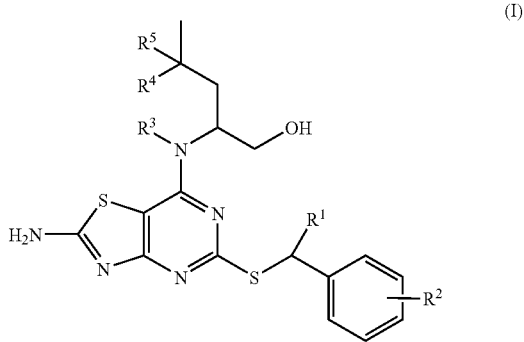 WO 02/076990, Example 37 | 156 | 1978 |
| 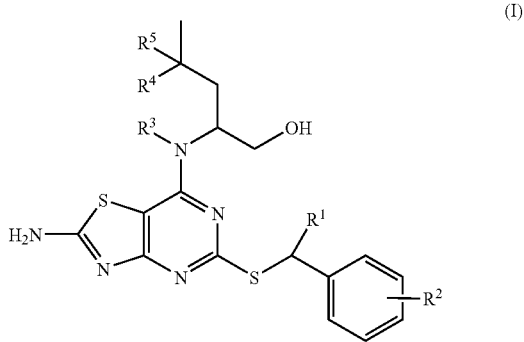 This application, Example 1 (b) | 592 | 540 |

The invention claimed is:

1. A compound of formula (I)

(I)

wherein $R^1$ is $CH_3$ or $CH_3CH_2$;

$R^2$ is H, 2-F, 2-Cl, 3-F, 3-$OCH_3$, 3-CN, 3-$CF_3$, 3-$CONH_2$ or 3-$SO_2CH_3$;

$R^3$ is H or $CH_3$;

$R^4$ is H or $CH_3$; and $R^5$ is H; or, when $R^4$ is $CH_3$, $R^5$ is H or F;

or pharmaceutically acceptable salts thereof.

2. A compound according to claim 1, or pharmaceutically acceptable salts thereof, wherein $R^5$ is F.

3. A compound according to claim 1, or pharmaceutically acceptable salts thereof, wherein $R^1$ is $CH_3$; $R^2$ is H, 2-F or 3-CN; $R^3$ is H; $R^4$ is H or $CH_3$; and $R^5$ is H.

4. A compound of formula (I) according to claim 1 which is:

- (2R)-2-[(2-amino-5-{[(1S)-1-(2-fluorophenyl)ethyl]thio}[1,3]thiazolo[4,5-d]pyrimidin-7-yl)amino]pentan-1-ol;
- (2R)-2-[(2-amino-5-{[(1S)-1-(2-fluorophenyl)ethyl]thio}[1,3]thiazolo[4,5-d]pyrimidin-7-yl)amino]-4-methylpentan-1-ol;
- (2R)-2-({2-amino-5-[(1-phenylethyl)thio][1,3]thiazolo[4,5-d]pyrimidin-7-yl}amino)-4-methylpentan-1-ol;
- (2R)-2-[(2-amino-5-{[(1R)-1-phenylethyl]thio}[1,3]thiazolo[4,5-d]pyrimidin-7-yl)amino]-4-methylpentan-1-ol;
- 3{(1S)-1-[(2-amino-7-{[(1R)-1-(hydroxymethyl)butyl]amino}[1,3]thiazolo[4,5-d]pyrimidin-5-yl)thio]ethyl}benzonitrile;
- (2R)-2-{[2-amino-5-({(1S)-1-[3-(methylsulfonyl)phenyl]ethyl}thio)[1,3]thiazolo[4,5-d]pyrimidin-7-yl]amino}-4-methylpentan-1-ol;
- (2R)-2-[(2-amino-5-{[(1S)-1-phenylethyl]thio}[1,3]thiazolo[4,5-d]pyrimidin-7-yl)amino]pentan-1-ol;
- 3{(1S)-1-[(2-amino-7-{[(1R)-1-(hydroxymethyl)-3-methylbutyl]amino}[1,3]thiazolo[4,5-d]pyrimidin-5-yl)thio]ethyl}benzonitrile;
- (2R)-2-({2-amino-5-[(1-phenylpropyl)thio][1,3]thiazolo[4,5-d]pyrimidin-7-yl}amino)-4-methylpentan-1-ol;
- 3-{1-[(2-amino-7-{[(1R)-1-(hydroxymethyl)-3-methylbutyl]amino}[1,3]thiazolo[4,5-d]pyrimidin-5-yl)thio]ethyl}benzamide;
- (2R)-2-{[2-amino-5-({1-[3-(trifluoromethyl)phenyl]ethyl}thio)[1,3]thiazolo[4,5-d]pyrimidin-7-yl]amino}-4-methylpentan-1-ol;
- (2R)-2-[{2-amino-5-[(1-phenylethyl)thio][1,3]thiazolo[4,5-d]pyrimidin-7-yl}(methyl)amino]-4-methylpentan-1-ol;
- (2R)-2-[(2-amino-5-{[1-(2-chlorophenyl)ethyl]thio}[1,3]thiazolo[4,5-d]pyrimidin-7-yl)amino]-4-methylpentan-1-ol;
- (2R)-2-[(2-amino-5-{[1-(3-methoxyphenyl)ethyl]thio}[1,3]thiazolo[4,5-d]pyrimidin-7-yl)amino]-4-methylpentan-1-ol;
- (2R)-2-[(2-amino-5-{[(1S)-1-phenylethyl]thio}[1,3]thiazolo[4,5-d]pyrimidin-7-yl)amino]-4-methylpentan-1-ol;
- (2R)-2-[(2-amino-5-{[(1S)-1-phenylethyl]thio}[1,3]thiazolo[4,5-d]pyrimidin-7-yl)amino]-4-fluoro-4-methylpentan-1-ol;
- (2R)-2-[(2-amino-5-{[(1S)-1-(2-fluorophenyl)ethyl]thio}[1,3]thiazolo[4,5-d]pyrimidin-7-yl)amino]-4-fluoro-4-methylpentan-1-ol; or
- (2R)-2-[(2-amino-5-{[(1S)-1-(3-fluorophenyl)ethyl]thio}[1,3]thiazolo[4,5-d]pyrimidin-7-yl)amino]-4-methylpentan-1-ol;

or a pharmaceutically acceptable salt thereof.

5. A pharmaceutical formulation comprising a compound of formula (l), as defined in claim 1, or a pharmaceutically acceptable salt thereof, in admixture with a pharmaceutically acceptable diluent or carrier.

6. (2R)-2-[(2-amino-5-{[(1S)-1-phenylethyl]thio}[1,3]thiazolo[4,5-d]pyrimidin-7-yl)amino]-4-methylpentan-1-ol, or a pharmaceutically acceptable salt thereof.

7. A pharmaceutical formulation comprising a compound according to claim 6, or a pharmaceutically acceptable salt thereof, in admixture with a pharmaceutically acceptable diluent or carrier.

8. A pharmaceutical formulation comprising at least one compound according to claim 3, or a pharmaceutically acceptable salt thereof, in admixture with a pharmaceutically acceptable diluent or carrier.

\* \* \* \* \*